United States Patent [19]

Naito et al.

[11] 4,278,675

[45] Jul. 14, 1981

[54] BRONCHODILATING PROCESS

[75] Inventors: Takayuki Naito, Kawasaki; Susumu Nakagawa, Tokyo; Tetsuro Yamasaki; Taka-aki Okita, both of Ichikawa; Haruhiro Yamashita, Tokyo, all of Japan

[73] Assignee: Bristol-Myers Company, New York, N.Y.

[21] Appl. No.: 74,847

[22] Filed: Sep. 13, 1979

[51] Int. Cl.³ .............................................. A61K 31/52
[52] U.S. Cl. ................................................... 424/253
[58] Field of Search ........................................ 424/253

[56] References Cited

U.S. PATENT DOCUMENTS

| 3,862,189 | 1/1975 | Schwender | 260/252 |
| 3,930,005 | 12/1975 | Wojnar et al. | 424/253 |
| 4,172,829 | 10/1979 | Naito et al. | 424/253 |

OTHER PUBLICATIONS

Montgomery et al.; J. Am. Chem. Soc., 80, 409–411, (1958).

Primary Examiner—Leonard Schenkman
Attorney, Agent, or Firm—Robert H. Uloth; Robert E. Carnahan

[57] ABSTRACT

A bronchodilating process employing purine derivatives "9-cyclohexyl-9H-adenine er 9-benzyl-2-n-propoxy-9H-adenine" is disclosed.

3 Claims, No Drawings

BRONCHODILATING PROCESS

BACKGROUND OF THE INVENTION

This invention concerns use of 9-cyclohexyl-9H-adenine or 9-benzyl-2-n-propoxy-9H-adenine in a bronchodilating process. Compounds of the instant process have non-adrenergic smooth muscle relaxant properties and are particularly valuable in overcoming acute bronchospasm and as adjuncts in symptomatic management of chronic, obstructive pulmonary diseases (e.g., asthma, bronchitis, emphysema).

Regarding types of non-adrenergic bronchodilators, the theophylline group of xanthine derivatives are particularly prominent. For instance, aminophylline, the ethylenediamine salt of theophylline, is an effective bronchodilator which may be administered parenterally, orally, or rectally and is useful in patients where direct relaxation of bronchial muscle is desired. Notwithstanding widespread use, the xanthine class of non-adrenergic bronchodilators have major disadvantages with respect to gastric irritation, cardiovascular and central nervous system side effects. Thus, there is a need for new and effective bronchodilators with increased potency and/or fewer or reduced untoward effects. Compounds employed in the instant process have been shown by standard pharmacological tests to be effective non-adrenergic bronchodilating agents with minimal cardiovascular and central nervous system effects.

Regarding prior art, 9-cyclohexyl-9H-adenine has been synthesized for use as a possible anticancer agent. It has also been tested as an anti-inflammatory and found to have no activity or activity of no practical value. As for 9-benzyl-2-n-propoxy-9H-adenine, this compound is believed to be novel although the corresponding "2-methoxy and 2-ethoxy" homologs reportedly have anti-inflammatory properties. The above prior art teachings are disclosed in the following references.

1. U.S. Pat. No. 3,930,005 (Wojnar, et al.) generically discloses inter alia compounds of the formula

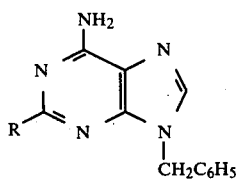

wherein R is (lower)alkoxy (e.g. specifically methoxy and ethoxy but no propoxy). The compounds are said to possess anti-inflammatory properties.

2. J. A. Montgomery, et al., J. Am. Chem. Soc., 80, 409–411 (1958) describes synthesis of the compound

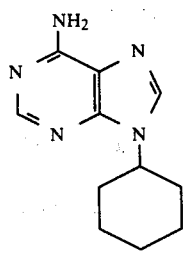

as a potential anti-cancer agent. The Wojnar, et al., patent supra teaches that the compound is relatively inactive as an anti-inflammatory agent.

3. U.S. Pat. No. 3,862,189 (Schwender) concerns compounds of the formula

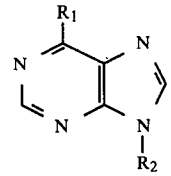

wherein, inter alia, $R_1$ is amino, alkylamino, aralkylamino, etc.; and $R_2$ is di-substituted phenylalkyl, tetrahydroquinoylalkyl, etc. reportedly useful as antianginal or bronchodilator agents.

SUMMARY AND DETAILED DESCRIPTION OF THE INVENTION

The compounds 9-cyclohexyl-9H-adenine or 9-benzyl-2-n-propoxy-9H-adenine are useful in the instant bronchodilating process in the free base form or as salts formed with pharmaceutically acceptable acids.

For the purpose of this disclosure, the term "pharmaceutically acceptable acid addition salt" denotes a salt form of 9-cyclohexyl-9H-adenine or 9-benzyl-2-n-propoxy-9H-adenine obtained by combination with a non-toxic inorganic or organic acid which is relatively nontoxic in anionic form. Examples of non-toxic pharmaceutically acceptable acid addition salts of the compounds of Formula I or II are those formed with sulfuric, hydrochloric, phosphoric, hydrobromic, hydroiodic, sulfamic, methanesulfonic, benzenesulfonic, para-toluene-sulfonic, acetic, lactic, succinic, malic, maleic, mucic, tartaric, citric, gluconic, benzoic, cinnamic, isethionic, fumaric, levulinic and related acids.

Preparation of non-toxic pharmaceutically acceptable acid addition salts of the compounds of the instant process is accomplished in conventional fashion by admixture of the base with at least one molecular equivalent of a selected acid in an inert organic solvent such as ethanol, benzene, ethyl acetate, ether, halogenated hydrocarbon and the like. Isolation of the salt is carried out by techniques known to the art such as inducing precipitation with a non-polar solvent (e.g., ether) in which the salt has limited solubility.

Preparation of 9-cyclohexyl-9Hadenine (I) is carried out by amination of 6-chloro-9-cyclohexylpurine (II) in a closed reaction vessel at 100°–120° C. with ethanolic ammonia as described by J. A. Montgomery, et al., J. Am. Chem. Soc., 80, 411 (1958). The reaction scheme below depicts this procedure along with alternate methods of preparation involving catalytic dehalogenation and reduction of 2-chloro-9-cyclohexyl-9H-adenine (III) or catalytic reduction of 6-amino-9-(2-cyclohexenyl)-9H-adenine (IV).

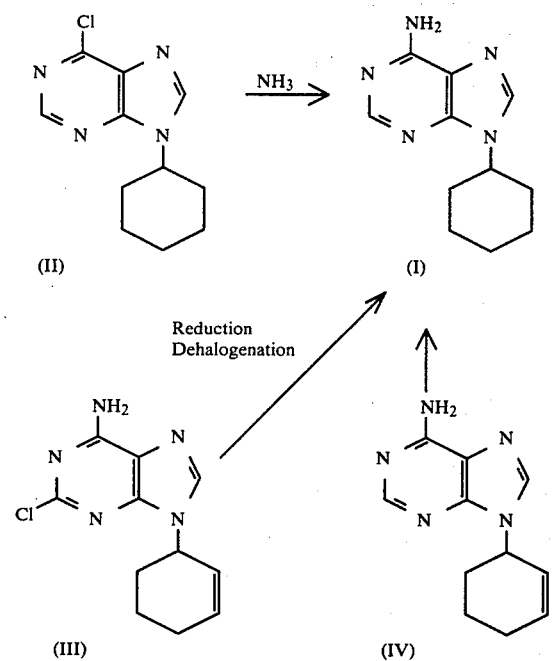

The requisite 2-chloro-9-(2-cyclohexenyl)-9H-adenine (III) starting material is obtained as described in allowed U.S. Pat. application Ser. No. 904,146 (issued Oct. 30, 1979 as U.S. Pat. No. 4,172,829) incorporated herein in its entirety by reference.

The compound "9-benzyl-2-n-propoxy-9Hadenine" is obtained by reaction 9-benzyl-2-chloro-9H-adenine with an alkali metal (e.g. sodium, potassium or lithium) n-propoxide in propanol or a reaction inert solvent such as benzene or toluene.

The bronchodilating process of the present invention comprises systemic administration to a mammal in need thereof an effective dose of from about 0.1 to 20 mg./kg. body weight of 9-cyclohexyl-9H-adenine or 9-benzyl-2-n-propoxy-9H-adenine or a pharmaceutically acceptable salt thereof. It is intended by systemic administration to include both oral and parenteral routes, e.g., intramuscular, intravenous, intraperitoneal and subcutaneous. Also, the active ingredient may be given by inhalation employing a suitable aerosol preparation. Oral administration is preferred.

Another aspect the present invention provides a pharmaceutical composition in dosage unit form useful for relief of bronchial constriction in mammals. The composition comprises, as the active ingredient, an effective bronchodilating amount of 9-cyclohexyl-9H-adenine or 9-benzyl-2-n-propoxy-9H-adenine or a pharmaceutically acceptable salt thereof in admixture with a pharmaceutically acceptable carrier or diluent.

The compounds of the present process may be administered either as individual therapeutic agents or as mixtures with other therapeutic agents. They may be administered alone, but are generally given in the form of pharmaceutical compositions. Examples of such compositions include tablets, lozenges, capsules, powders, aerosol sprays, aqueous or oily suspensions, syrups, elixirs, and aqueous solutions.

The nature of the pharmaceutical composition and the pharmaceutical carrier or diluent will, of course, depend on the desired route of administration. For example, oral compositions may be in form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations may be in the form of aqueous or oily suspensions, solutions, emulsions, syrups, elixirs, etc. or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of the active ingredients of the instant process with conventional pharmaceutical vehicles may be employed, e.g. as an aerosol spray for inhalation, as an aqueous solution for intravenous injection or as an oily suspension for intramuscular injection.

The compounds, pharmaceutical compositions and bronchodilating use thereof constituting embodiments of this invention are more fully illustrated by the following examples.

EXAMPLE 1

9-Cyclohexyl-9H-adenine

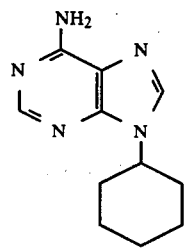

Method A.

A mixture of 2-chloro-9-(2-cyclohexenyl)adenine (252 mg., 1 mmole) in 15 ml. of ethanol is hydrogenated for 2 days with 93 mg. of 10% palladium-on-charcoal and filtered. Evaporation of the filtrate in vacuo and purification of the residue by silica gel chromatography using $CHCl_3$—MeOH affords 33 mg. (14%) of 9-cyclohexyl-9H-adenine, m.p. 196°–201° C. IR (KBr): 3300, 3250, 2930, 1665, 1595, 1565, 1470, 1410, 1300 $cm^{-1}$. UV:$\lambda_{max}^{EtOH}$ 262 nm ($\epsilon$13,300). NMR($CDCL_3$):$\delta$1.80(10H,m), 4.40(1H,m), 6.05(2H,s), 7.78(1H,s), 8.26(1H,s).

Method B.

Reaction of 6-chloro-9-cyclohexylpurine in ethanol saturated with ammonia in a sealed tube for 15 hrs. at 105°–110° C. as described by J. A. Montgomery, et al., J. Am. Chem. Soc., 80, 411 (1958) affords the title compound.

EXAMPLE 2

9-Benzyl-2-n-propoxy-9H-adenine

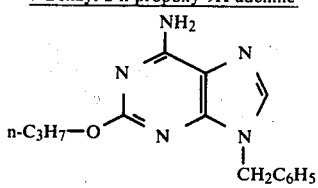

A. 9-Benzyl-2,6-dichloro-9H-purine.

To a stirred solution of 2,6-dichloropurine (2.8 g., 15 mmole) in 50 ml. of dry N,N-dimethylformamide is added 50% sodium hydride (1.44 g., 30 mmole) and 5.5 ml. of benzyl bromide at ambient temperature. The mixture is stirred for 1 hr. at room temperature, treated with water and filtered to remove insolubles. The filtrate is neutralized with sodium hydroxide solution and evaporated in vacuo. Residual material thus obtained is extracted with $CHCl_3$ and the $CHCl_3$ extracts evaporated in vacuo to give an oil. Purification of the oil by chromatography on a silica gel column using $CHCl_3$—MeOH as eluent affords 856 mg. (21%) of 9-benzyl-2,6-dichloro-9H-purine as colorless needles (crystallized from ethanol), m.p. 146°–147° C. IR(KBr): 1600, 1560, 1365, 1235, 1150 cm$^{-1}$. UV:$\lambda_{max}^{EtOH}$ 275 nm($\epsilon$9,400). NMR(CDCl$_3$):$\delta$5.32(2H,s), 7.21(5H,m), 7.93(1H,s).

Anal. Calcd. for $C_{12}H_8N_4Cl_2 \cdot 1/10C_2H_5OH$: C, 51.64; H, 3.06; N, 19.75; Cl, 24.99. Found: C, 52.05; H, 2.72; N, 19.92; Cl, 24.61.

B. 9-Benzyl-2-chloro-9H-adenine.

A mixture of 9-benzyl-2,6-dichloro-9H-adenine (500 mg., 1.9 mmole) and 5 ml. of methanol saturated with ammonia in the cold is heated at 100° C. for 6 hrs. in a sealed tube. Evaporation of the reaction mixture in vacuo affords 437 mg. 94%) of 9-benzyl-2-chloro-9H-adenine, m.p. 228°–229° C. IR(KBr): 3475, 3080, 1645, 1595, 1570, 1315, 1260 cm$^{-1}$. UV:$\lambda_{max}^{EtOH}$ 266 nm($\epsilon$15,000). NMR(DMSOd$_6$):$\delta$5.28(2H,s), 7.20(5H,m), 7.65(2H,br.s), 8.13(1H,s).

Anal. Calcd. for $C_{12}H_{10}N_5Cl$: C, 55.50; H, 3.88; N, 26.97; Cl, 13.56. Found: C, 55.52; H, 3.66; N, 27.52; Cl, 13.74.

According to Example 1 of U.S. Pat. No. 3,930,005, 9-benzyl-2-chloro-9H-adenine (reportedly melting at 158°–160° C.) can also be prepared by alkylating 2-chloroadenine with benzyl chloride in the presence of potassium carbonate in dimethylacetamide.

C. 9-Benzyl-2-n-propoxy-9H-adenine.

A mixture of 9-benzyl-2-chloro-9H-adenine (130 mg., 0.5 mmole) and 1.25 ml. of 1 N sodium n-propoxide in n-propanol in 13 ml. of n-propanol is refluxed overnight, neutralized with hydrochloric acid and evaporated in vacuo. Trituration of residual material with water provides 118 mg. of crude product which crystallized from aqueous ethanol affords 90 mg. (64%) of analytically pure 9-benzyl-2-n-propoxy-9H-adenine, m.p. 178°–180° C. (dec.). IR(KBr): 3280, 3130, 2970, 1660, 1595, 1405, 1350, 1330, 1275 cm$^{-1}$. UV:$\lambda_{max}^{EtOH}$ 254 nm($\epsilon$8,800), 269.5 nm($\epsilon$12,800). NMR(CDCl$_3$):$\delta$1.02(3H,t,J=7 Hz), 1.6-2.1(2H,m), 4.25(2H,t,J=7 Hz), 5.20(2H,s), 6.00(2H,br.s), 7.23(5H,m), 7.50(1H,s).

Anal. Calcd. for $C_{15}H_{17}N_5O$: C, 63.58; H, 6.05; N, 24.72. Found: C, 63.43; H, 6.01; N, 24.25.

EXAMPLE 3

Pharmacological Evaluation

A. In Vitro Bronchodilator Activity.

Tracheal chains of guinea pig were prepared by the method of A. Akcasu, Arch. Int. Pharmcodyn. Ther., 122, 201 (1959). The response to each test compound was recorded by the Magnus method and expressed as a percentage of the maximum response obtained with 0.1 mcg./ml. of isoproterenol prior to each experiment. Bronchodilator activity (in vitro) of aminophylline and compounds of the instant process is expressed below as an $EC_{50}$ value (concentration in mcg./ml. which produces a relaxation which is 50% of the maximum response to 0.1 mcg./ml. of isoproterenol).

| In Vitro Test Results | |
| --- | --- |
| Compound of Example | $EC_{50}$ (mcg./ml.) |
| 9-Cyclohexyl-9H-adenine | 0.91 |
| 9-Benzyl-2-n-propoxy-9H-adenine | 0.34 |
| Aminophylline | 16.6 |

B. In Vivo Bronchodilator and Hypotensive Activity.

The in vivo bronchodilator activity of aminophylline and test compounds was evaluated according to a modification of the mthod described by L. G. W. James, J. Pharm. Pharmac., 21, 379 (1969) by measuring decrease in intratracheal pressure (ITP) in the guinea pig. The trachea of anesthetized guinea pig was cannulated and the ITP recorded on a polygraph under artificial ventilation. Arterial blood pressure (ABP; reflecting hypotensive activity) was also measured during the experiment. Either intravenous or intraduodenal routes of administration are used. Results set forth below express the bronchodilator activity (ITP) as an $ED_{50}$ value (dose in mg./kg. resulting in a 50% decrease in intratracheal pressure) and the hypotensive activity (ABP) as an $ED_{20}$ value (dose in mg./kg. which reduces arterial blood pressure by 20%). The ratio of hypotensive $ED_{20}$/bronchodilating $ED_{50}$ reflects an assessment of the separation of desirable bronchodilator activity from undesirable cardiovascular (hypotensive) effect in the compounds. The larger the ABP/ITP ratio, the greater separation of bronchodilator activity and hypotensive side effect.

| | Intravenous Test Results | | |
| --- | --- | --- | --- |
| Compound of Examples | (mg./kg.) | | Ratio |
| | ITP $ED_{50}$ | ABP $ED_{20}$ | ABP/ITP |
| 9-Cyclohexyl-9H-adenine | 0.24 | >3 | >1.2 |
| 9-Benzyl-2-n-propoxy-9H-adenine | 0.83 | 1.7 | 2.0 |
| Aminophylline | 0.58 | 1.4 | 2.4 |

EXAMPLE 4

Pharmaceutical Compositions

A. Tablets.

The compounds of Formula I are compounded into tablets according to the following example:

| Materials | Amount |
| --- | --- |
| 9-Cyclohexyl-9H-adenine | 20.0 g. |
| Magnesium stearate | 1.3 g. |

-continued

| Materials | Amount |
| --- | --- |
| Corn starch | 12.4 g. |
| Corn starch, pregelatinized | 1.3 g. |
| Lactose | 215.0 g. |

The foregoing materials are blended in a twin-shell blender and then granulated and pressed into tablets employing 250 mg. each. Each tablet contains about 20 mg. of active ingredient. The tablets may be scored and quartered so that unit doses of 5.0 mg. of active ingredient may be conveniently obtained.

B. Capsules.

The purine derivatives of Formula I are compounded into capsules according to the following example:

| Materials | Amount |
| --- | --- |
| 9-Cyclohexyl-9H-adenine | 50.0 g. |
| Lactose | 221.0 g. |

-continued

| Materials | Amount |
| --- | --- |
| Magnesium stearate | 4.0 g. |

The foregoing materials are blended in a twin-shell blender and No. 1 hard gelatin capsules filled with 275 mg. of the blended composition. Each capsule contains 50 mg. of active ingredient.

What is claimed is:

1. A bronchodilating method which comprises systemic administration to a mammal in need thereof an effective dose of from about 0.1 to 20 mg./kg. body weight of a compound selected from the group consisting of 9-cyclohexyl-9H-adenine, 9-benzyl-2-n-propoxy-9H-adenine and a pharmaceutically acceptable acid addition salt thereof.

2. The method as claimed in claim 1 wherein the active ingredient is 9-cyclohexyl-9H-adenine or a pharmaceutically acceptable acid addition salt thereof.

3. The method as claimed in claim 1 wherein the active ingredient is 9-benzyl-2-n-propoxy-9H-adenine or a pharmaceutically acceptable acid addition salt thereof.

* * * * *